United States Patent [19]

Fost et al.

[11] Patent Number: 5,496,478
[45] Date of Patent: Mar. 5, 1996

[54] SILICONE CONTAINING IMIDAZOLINE COMPOSITIONS

[75] Inventors: Dennis L. Fost, Ridgewood; Abe Berger, Summit, both of N.J.

[73] Assignee: Mona Industries, Inc., Paterson, N.J.

[21] Appl. No.: 304,563

[22] Filed: Sep. 12, 1994

[51] Int. Cl.$^6$ .................... C10M 105/08; C07D 231/10
[52] U.S. Cl. .................. 252/33.6; 252/9; 252/11; 252/12; 252/42.7; 252/49.6; 252/49.7; 252/50; 252/51.5 R; 514/63; 548/110
[58] Field of Search .................. 548/110; 514/63; 252/9, 11, 12, 42.7, 49.6, 49.7, 50, 51.5 R, 33.6

[56] References Cited

U.S. PATENT DOCUMENTS 3,506,674  4/1970  Berger .................. 260/294.8
3,558,556  1/1971  Berger et al. .................. 260/46.5

*Primary Examiner*—Joseph K. McKane
*Attorney, Agent, or Firm*—Franklyn Schoenberg

[57] ABSTRACT

Silicone containing imidazoline compositions are provided which are represented by the formula:

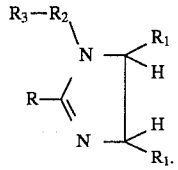

4 Claims, No Drawings

SILICONE CONTAINING IMIDAZOLINE COMPOSITIONS

FIELD OF THE INVENTION

The present invention relates to novel imidazoline compositions and, more particularly, to silicone containing imidazoline compositions and to methods for preparing the same.

BACKGROUND OF THE INVENTION

The production and marketing of imidazolines and various derivatives thereof has been carried on for a number of years. Such compositions have been widely used as surface active agents, metal treating compounds and a variety of other applications. Imidazolines are commonly prepared by condensing, under conditions of heating and stirring, a long chain aliphatic monocarboxylic or fatty acid or a source thereof such as amides (or esters of such acids) with an alkyl, hydroxyalkyl and/or aminoalkyl ethylene diamine derivative, such as hydroxyethyl ethylene diamine.

Organosiloxane compositions including carboxylfunctional siloxane and other silicone compositions which exhibit excellent properties as surface active agents, lubricants and the like are also known and have been used commercially over the years. While a variety of imidazoline and polysiloxane compositions and derivatives thereof are known, to the best of our knowledge there has been no disclosure or suggestion of the novel silicone-containing imidazoline compositions and methods for preparing the same herein described.

SUMMARY OF THE INVENTION

It is accordingly an object of the present invention to provide highly useful, novel silicone containing imidazoline compositions and the acid salts thereof.

It is a further object of the present invention to provide a method for directly and readily preparing silicone containing imidazoline compositions and the acid salts thereof.

In accordance with the present invention there are provided novel silicone containing imidazoline compositions that may be represented by the formula:

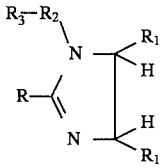

wherein:
R is an organosilicone backbone chain which may be represented by the formula:

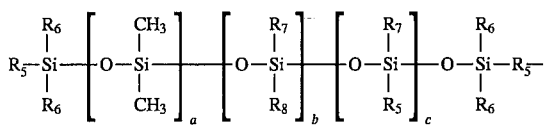

wherein:
$R_5$, which can be the same or different, can be selected from $R_6$, a group of the formula $-\{CH_2\}_{n1}-B_{n2}-(CH_2)_{n3}-$ and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is a group of the formula $-(CH_2)_{n1}-B_{n2}-(CH_2)_{n3}-$ $R_6$ can be the same or different and can be selected from alkyl, aryl and olefin (vinyl);

$R_7$ and $R_8$, which can be the same or different, are selected from alkyl, aryl, capped or uncapped polyoxyalkylene, alkaryl, aralkylene and alkenyl (vinyl);

a can be an integer of 0 to 50,000;

b can be an integer of 0 to 5,000; and c can be an integer of 0 to 100;

$R_1$ which can be the same or different is of the group consisting of hydrogen and lower alkyl;

$R_2$ is hydrogen or an alkylene hydrocarbon group; and $R_3$ can be selected from $-OH$, $-NH_2$, $R_9CONH-$, $R_9COO-$ and $-H$, wherein $R_9$ is saturated or unsaturated alkyl having from 1-22 carbon atoms.

The present invention is also concerned with acid salts of silicone-containing imidazoline compositions having anionic groups of valences from 1 to 3 which may be represented by the formula:

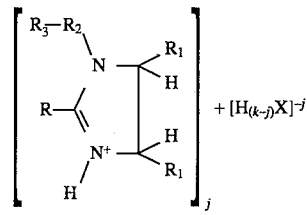

wherein:
R is as hereinabove defined;
$R_1$ and $R_2$ are as hereinabove described;
$R_3$ is as hereinabove defined;
X is an anion group having 1–3 valence;
j is an integer from 1 to 3; and
k is an integer from 1–3; with the proviso that (k–j) is 0 or a positive integer.

In another aspect of the present invention, there is also provided a method for readily preparing silicone-containing imidazoline compositions having effective surface active, substantivity, corrosion inhibition and lubrication properties which comprises reacting an organosilicone fluid or composition having at least one terminal, lateral or combination of terminal and lateral carboxyl functional groups with at least a stoichiometric amount of an alkyl, hydroxyalkyl and/or aminoalkyl ethylene diamine derivative at an elevated temperature, preferably at least about 140° C., for a time necessary to react the carboxyl functional group and provide for the cyclization of the reaction product.

DESCRIPTION OF THE PREFERRED EMBODIMENT

The present invention is concerned with novel and highly useful silicone-containing imidazoline compositions that can be represented by the formula:

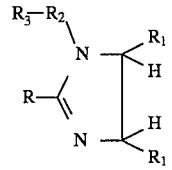

wherein:

R is an organosilicone backbone chain which may be represented by the formula:

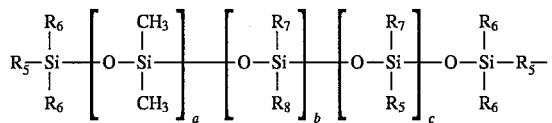

wherein:

$R_5$, which can be the same or different, can be selected from $R_6$, a group of the formula $-(CH_2)_{n1}-B_{n2}-(CH_2)_{n3}-$ and mixtures thereof, wherein $R_6$ is as herein below defined, $n^2$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is a group of the formula $-(CH_2)_{n1}-B_{n2}-(CH_2)_{n3}-$ $R_6$ can be the same or different and can be selected from alkyl, aryl and olefin (vinyl);

$R_7$ and $R_8$, which can be the same or different, are selected from alkyl, aryl, capped or uncapped polyoxyalkylene, alkaryl, aralkylene and alkenyl (vinyl);

a can be an integer of 0 to 50,000;

b can be an integer of 0 to 5,000; and c can be an integer of 0 to 100;

$R_1$, which can be the same or different is of the group consisting of hydrogen and lower alkyl;

$R_2$ is hydrogen or an alkylene hydrocarbon group; and $R_3$ can be selected from $-OH$, $-NH_2$, $R_9CONH-$, $R_9COO-$ and H, wherein $R_9$ is saturated or unsaturated alkyl having from 1-22 carbon atoms.

The novel imidazoline compositions of the present invention can be prepared by condensing, under conditions of heating and stirring either neat or in a solvent, a polysiloxane composition or fluid having at least one carboxyl functional group as is described in detail hereinafter (or a source thereof such as amides or esters of the acids) with an hydroxylalkyl ethylene diamine derivative, such as hydroxyethyl ethylene diamine. The mole ratio of the carboxyl functional polysiloxane composition to the diamine is variable but generally falls within the range of 1 mole of the carboxyl functional silicone composition to 1 to about 2 moles preferably about 1.1 to 1.6 moles of the diamine, followed by removal of excess diamine by distillation etc., and the temperature at which the condensation reaction is carried out is generally in excess of 100° C., usually in the range of about 120° C. to about 250° C. or 300° C., preferably greater than 140° C. The reaction time is several hours, usually within the range of about 4 to 12 hours, depending upon the particular reactants employed and the particular condensation temperature employed; or, where the reaction is carried out under less that atmospheric pressure, the reaction temperature may be somewhat reduced. Usually, the condensation temperature or temperature of heating and the duration of the heating are so correlated as to cause splitting out of water in excess of 1.5 moles, preferably 2 moles, for each mole of carboxyl group. In the case of complete reaction of the carboxyl groups, 2 moles of water will be evolved to form the product with an imidazoline nucleus.

The polysiloxane composition or fluids containing functional carboxyl groups or derivatives thereof (terminal, lateral or combination of terminal and lateral) applicable for use in preparing the silicone-containing imidazoline compositions of the invention can be prepared by a variety of known procedures such as illustrated by the following:

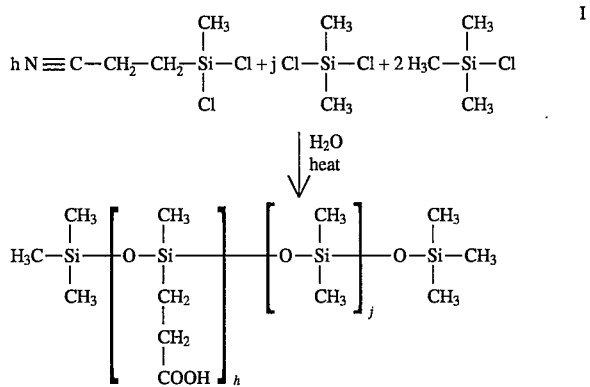

wherein:

h is an integer from 1–100;

j is an integer from 0–1000.

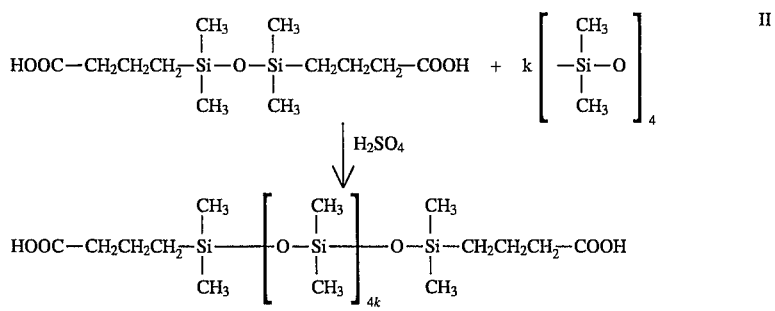

wherein:

k is an integer from 1–1000.

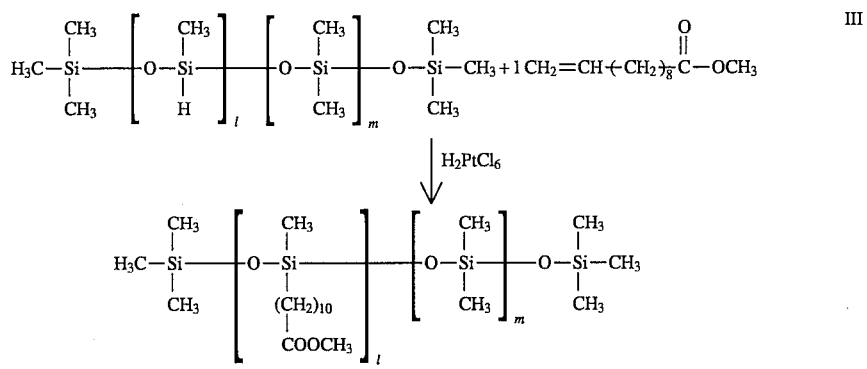

wherein:
l is an integer from 1–100;
m is an integer from 0–1000.

Suitable carboxyl functional siliconecompositions having terminal, lateral or combinations of terminal and lateral functional groups are available commercially,, for example, from Shin-Etsu. While the molecular weight of the silicone compositions which may be employed is not critical, and suitable compositions may have carboxyl equivalent weights of 8000, or even higher, silicone compositions having carboxyl equivalent weights from about 1500 to about 6000 are in general preferred.

The hydroxyalkyl diamines or functional alkyl diamines, notably the lower functional hydroxy alkylene diamine, which are used to produce the imidazoline compositions of the invention, can likewise be selected from large numbers of known examples thereof, including aminoethylethanolamine or beta-hydroxyethyl ethylenediamine, aminoethyl ethylenediamine. N-methyl ethylene diamine, N-ethyl ethylene diamine and the like.

The novel acid salts of the silicone-containing imidazoline compositions of the invention can be represented by the following formula:

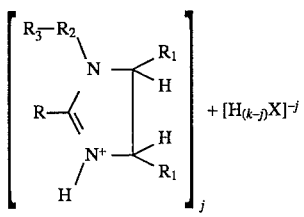

wherein:
R is an organosilicone backbone chain as hereinabove defined;
$R_1$ and $R_2$ are as hereinabove described;
$R_3$ is as hereinabove defined;
X is an anion group having 1–3 valence;
j is an integer from 1 to 3; and
k is an integer from 1–3; with the proviso that (k–J) is 0 or a positive integer.

The acid salts of the aforementioned silicone-containing imidazoline compositions of the invention are readily prepared by simply admixing the imidazoline composition and an organic or mineral acid as illustrated below at temperatures between about room temperature and about 100° C., and preferably at ambient temperatures in the range of about 20° to 30° C. The imidazoline composition and acid are desirably combined in approximately stoichiometric proportions, sufficient acid being added to substantially neutralize the amine groups present in the imidazoline composition:

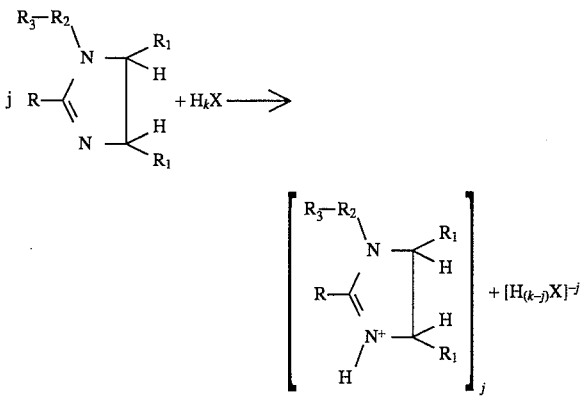

Illustrative of such suitable mineral and organic acids are phosphoric acid, phosphorous acid, sulfuric acid, sulfurous acid, hydrochloric acid, hypochlorous acid, acetic acid, carbonic acid, nitric acid, formic acid.

The imidazoline compositions of the present invention and acid salts thereof lend themselves to a wide variety of practical applications. Such materials can be employed for example, as emulsifier and dispersing agents, wetting agents and as additives to surface active compositions. They are also useful to provide improved substantively to a variety of surfaces, as antistatic agents, foam stabilizers, as useful additives for metal cleaning and treating compositions and can be used to improve the lubricating and corrosion inhinition properties for metal treating compositions and in a variety of personal treating and cosmetic compositions.

Various other materials can be added to the novel silicone-containing imidazoline composition of the preset invention and the acid salts thereof. For example, such additives include various surface active agents; alkaline builder salts and agents such as sodium carbonate, sodium bicarbonate, sodium sulfate and the like, as well as special purpose additives such as dyes, bleaches, brighteners and the like.

The invention is further illustrated by the following examples which are not to be considered as limitative of its scope.

EXAMPLE 1

A Trimethylsilyl capped carboxylpropyl containing silicone fluid obtained from Shin-Etsu under the trade designation X-22 371 is used in this example. The silicone fluid contains 8.01% carboxyl groups (number of grams of fluid/carboxyl group=561.79).

134.8 grams (0.24 equivalent weight) the silicone fluid and 31.5 grams of aminoethyl ethanolamine (0.3 mole) are charged to a reaction vessel and heated to about 150° under nitrogen whereupon volatiles begin distilling off. The reaction mixture is heated for 3 hours over which time 14.5 ml of volatiles are collected which separates into 2 layers. The bottom layer of 4 ml is water. The alkali number of the reaction mixture at this time is 121.9 (theory 121.3).

A vacuum to about 10 mm is slowly applied to the reaction vessel while the temperature is raised to 165° C. as more volatiles are collected and the reaction mixture becomes very viscous. The reaction mixture is then heated at 195° C. for two additional hours.

After cooling an amber liquid is obtained having an alkali number of 95 (theory –89).

EXAMPLE 2

A Trimethylsilyl capped carboxylpropyl containing silicone fluid obtained from Shin-Etsu under the designation X-223710 is used in this example. The silicone fluid has a carboxyl content of 3.0% (number of grams of fluid/carboxyl group=1500).

100 grams (0.067 equivalents) of the silicone fluid is combined with 10.5 grams (excess) of aminoethyl ethanolamine and 50 ml of xylene in a reaction vessel. The reaction mixture is heated to reflux, removing water azeotropically as it is formed. The temperature of the refluxing reaction mixture is in the range of 165°–170° C.

After a period of four hours a total of 2.5 ml of water somewhat contaminated with alkanoamine is collected. The reaction mixture is held under a vacuum of 30 mm to remove the xylene and then the vacuum is reduced to 5 mm while raising the temperature of the reaction vessel to 195° C. The reaction mixture is heated at 195° C. for 3 hours.

When cooled, an amber liquid is obtained having an alkali number of 44 (theory 36). An infra red scan of the reaction product is consistent with an imidazoline structure.

EXAMPLE 3

An alpha-omega Bis-carboxylalkyl Dimethylsilyl capped dimethylpolysiloane fluid obtained from Shin-Estu under the designation X-22162A is used in this example. The silicone fluid has a carboxyl content of 4.6% which corresponds to a molecular weight of 1956.

A combination of 97.8 grams (0.05 mole) of the above silicone fluid, 15.6 grams (0.15 mole—50% excess) of aminoethyl ethanolamine and 50ml of xylene is prepared in a reaction vessel and heated to reflux (about 170° C.). The reaction mixture is heated under reflux for 6 hours during which time 4.5 ml of water is collected (theory—3.6).

The reaction mixture is cooled to about 80° C. and a vacuum of 30 mm is applied to remove the solvent xylene. The reaction mixture is slowly raised to 200° C. while slowly reducing the pressure to a vacuum of about 3 mm during which time unreacted aminoethyl ethanolamine is removed and complete cyclization of the reaction product occurs.

The reaction product is an orange liquid having an alkali number of 61 (theoretical 53.6) and an infra red scan confirms the structure of the reaction product as being consistent with imidazoline.

EXAMPLE 4

A trimethylsilyl capped carboxylalkyl thioalkyl containing silicone fluid obtained from Dow Corning under the designation Q2-7119 is used in this example. The silicone fluid has an acid number of 20.5 which corresponds to an equivalent weight (grams of fluid per carboxyl group) of 2736.

273.6 grams (0.1 equivalent) of the silicone fluid is combined with 15.7 grams (an excess) of aminoethyl ethanolamine and 75 ml of xylene in a reaction vessel and heated to reflux. After heating 8 hours at reflux (175°–180° C.), 3.9 ml of water is collected (theoretical 3.6). Heating the reaction mixture is continued under a vacuum of 30 mm to remove the xylene after while the temperature of the reaction mixture is raised to 200° C. which the pressure is reduced to 5 mm vacuum. After 3 hours, all excess aminoethyl ethanolamine is removed from the reaction mixture and cyclization is completed.

Upon cooling, a yellow viscous liquid reaction product is obtained having an alkali number of 25 (theory 20) and an infra red scan of the reaction product shows a band of 6.25 microns consistent with an imidazoline ring.

EXAMPLE 5

The silicone fluid of example 2 is used in this example.

150 grams of the silicone fluid is combined with 15 grams of aminoethyl ethylenediamine and 50 ml of xylene in a reaction vessel and heated for 6 hours at a temperature of 170°–180° C. during which time 4 ml of volatiles are collected. The solvent and excess aminoethyl ethylenediamine is then removed from the reaction mixture by heating for 3 hours at a temperature of 195° C. under a high vacuum.

The reaction product has a structure consistent with imidazoline as confirmed by an infra red scan and alkali number determination.

EXAMPLE 6

The reaction product (silicone-containing imidazoline) of example 2 is used in this example.

127.5 grams of the silicone-containing imidazoline composition is dissolved in 150 ml of isopropanol in a reaction vessel and 5.56 grams of 85% phosphoric acid (0.05 mole) is added drop-wise to the solution with good agitation at ambient temperature. A clear yellow solution is obtained having a alkali number of zero.

Although some preferred embodiments have been described, many modifications and variations may be made thereto in light of the above teachings. It is therefore to be understood that within the scope of the appended claims, the invention maybe practiced otherwise than as specifically described and illustrated.

What is claimed is:

1. Silicone containing imidazoline compositions represented by the formula:

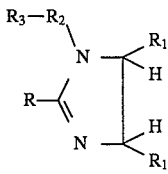

wherein:

R is a organosilicone chain represented by the formula:

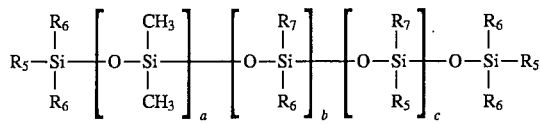

wherein:

$R_5$, which can be the same or different, is selected from $R_6$, a group of the formula $(CH_2)_{n1}-B_{n2}-(CH_2)_{n3}-$ and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is a group of the formula $-(CH_2)_{n1}-B_{n2}-(CH_2)_{n3}-$;

$R_6$, which can be the same or different is selected from alkyl, aryl and olefin;

$R_7$ and $R_8$, which can be the same or different are selected from alkyl, aryl, polyoxyalkylene, alkaryl, aralkylene and alkenyl;

a is an integer from 0 to 50,000;

b is an integer from 0 to 5,000; and c is an integer from 0 to 100;

$R_1$ which can be the same or different is of the group consisting of hydrogen and lower alkyl;

$R_2$ is hydrogen or an alkylene hydrocarbon group; and $R_3$ is selected from $-OH$, $-NH_2$, $R_9CONH-$, $R_9COO-$ and $-H$, wherein $R_9$ is saturated or unsaturated alkyl having from 1–22 carbon atoms.

2. Acid salts of silicone-containing imidazoline represented by the following formula:

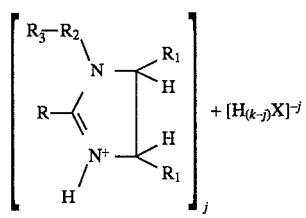

wherein:

R is a organosilicone chain represented by the formula:

wherein:

$R_5$, which can be the same or different, is selected from $R_6$, a group of the formula $-(CH_2)_{n1}-B_{n2}-(CH_2)_{n3}-$ and mixtures thereof, wherein $R_6$ is as herein below defined, $n^1$ is zero or an integer from 1 to 12, $n^2$ is 0 or 1, $n^3$ is an integer from 1 to 5, and B is sulfur or oxygen with the proviso that when $n^2$ is 1, $n^1$ and $n^3$ each is at least 1; and with the further proviso that at least one of $R_5$ is group of the formula $-(CH_2)_{n1}-B_{n2}-(CH_2)_{n3}-$;

$R_6$, which can be the same or different is selected from alkyl, aryl and olefin;

$R_7$ and $R_8$, which can be the same or different, are selected from alkyl, aryl, polyoxyalkylene, alkaryl, aralkylene and alkenyl;

a is an integer from 0 to 50,000;

b is an integer from 0 to 5,000; and c is an integer from 0 to 100;

$R_1$ which can be the same or different is of the group consisting of hydrogen and lower alkyl;

$R_2$ is hydrogen or an alkylene hydrocarbon group;

$R_3$ is selected from $-OH$, $-NH_2$, $-R_9CONH$, $R_9COO-$ and $-H$ wherein $R_9$ is saturated or unsaturated alkyl having from 1–22 carbon atoms;

X is an anion group having 1–3 valence.

j is an integer from 1 to 3; and k is an integer from 1 to 3; with the proviso that (k–j) is 0 or a positive integer.

3. The silicone containing imidazoline compositions as claimed in claim 1, wherein the terminal $R_5$ groups are $R_6$ groups.

4. The acid salts of silicone-containing imidazolines as claimed in claim 2, wherein the terminal $R_5$ groups are $R_6$ groups.

* * * * *